US009605167B2

(12) United States Patent
Gazaway et al.

(10) Patent No.: US 9,605,167 B2
(45) Date of Patent: Mar. 28, 2017

(54) HEAT SENSITIVE TAMPER INDICATING MARKINGS (71) Applicant: SICPA HOLDING SA, Prilly (CH)

(72) Inventors: Toni Lee Gazaway, Stafford, VA (US); Thomas Classick, Fairfax Station, VA (US); John Vereen, Alexandria, VA (US); Hau Lieu, Annandale, VA (US)

(73) Assignee: SICPA HOLDING SA, Prilly (CH)

( * ) Notice: Subject to any disclaimer, the term of this patent is extended or adjusted under 35 U.S.C. 154(b) by 261 days.

(21) Appl. No.: 14/301,883

(22) Filed: Jun. 11, 2014

(65) Prior Publication Data

US 2014/0368821 A1    Dec. 18, 2014

Related U.S. Application Data (60) Provisional application No. 61/834,201, filed on Jun. 12, 2013.

(51) Int. Cl.
| B41M 3/14 | (2006.01) |
| B42D 25/378 | (2014.01) |
| C09D 11/037 | (2014.01) |
| C09D 11/50 | (2014.01) |
| G01N 21/71 | (2006.01) |
| G01N 21/78 | (2006.01) |

(52) U.S. Cl.
CPC .............. *C09D 11/037* (2013.01); *B41M 3/14* (2013.01); *B42D 25/378* (2014.10); *C09D 11/50* (2013.01); *G01N 21/71* (2013.01); *G01N 21/78* (2013.01); *B42D 2033/26* (2013.01); *Y10T 428/24901* (2015.01)

(58) Field of Classification Search
CPC ...... C09D 11/037; C09D 11/50; G01N 21/78; G01N 21/71; Y10T 428/24901; B41M 3/14; B42D 25/378; B42D 2033/26
See application file for complete search history.

(56) References Cited

U.S. PATENT DOCUMENTS

| 3,615,972 | A | 10/1971 | Morehouse et al. |
| 3,945,956 | A | 3/1976 | Garner et al. |
| 4,287,308 | A | 9/1981 | Nakayama et al. |
| 4,705,356 | A | 11/1987 | Berning et al. |
| 4,721,271 | A | 1/1988 | Goldstein et al. |
| 4,838,648 | A | 6/1989 | Phillips et al. |
| 5,084,351 | A | 1/1992 | Philips et al. |
| 5,211,877 | A | 5/1993 | Andrejewski et al. |
| 5,214,530 | A | 5/1993 | Coombs et al. |
| 5,281,480 | A | 1/1994 | Phillips et al. |
| 5,362,315 | A | 11/1994 | Muller-Rees et al. |
| 5,383,995 | A | 1/1995 | Phillips et al. |
| 5,536,756 | A | 7/1996 | Kida et al. |
| 5,569,535 | A | 10/1996 | Phillips et al. |
| 5,571,624 | A | 11/1996 | Phillips et al. |
| 6,235,394 | B1 | 5/2001 | Shimazawa et al. |
| 6,235,800 | B1 | 5/2001 | Kyuno et al. |
| 6,410,130 | B1 | 6/2002 | Schuhmacher et al. |
| 6,423,246 | B1 | 7/2002 | Kasch et al. |
| 6,509,384 | B2 | 1/2003 | Kron et al. |
| 6,531,221 | B1 | 3/2003 | Schuhmacher et al. |
| 6,582,781 | B1 | 6/2003 | Schuhmacher et al. |
| 6,732,961 | B2 | 5/2004 | Leigeber et al. |
| 6,838,166 | B2 | 1/2005 | Phillips et al. |
| 7,232,607 | B2 * | 6/2007 | Satake ................ B01J 13/14 428/402.22 |
| 2001/0044014 | A1 | 11/2001 | Miyata et al. |
| 2006/0102307 | A1 | 5/2006 | Kron et al. |
| 2013/0014690 | A1 | 1/2013 | Shirase |

FOREIGN PATENT DOCUMENTS

| EP | 486080 | 10/1991 |
| EP | 0 601 483 | 6/1994 |
| EP | 686 675 | 12/1995 |
| EP | 1 046 692 | 10/2000 |
| EP | 1 213 338 | 6/2002 |
| WO | 02/073250 | 9/2002 |
| WO | 03/000801 | 1/2003 |

(Continued)

OTHER PUBLICATIONS

Author Unknown, "Expancel Microspheres, An Introduction", Boud Minerals, date of publication unknown, obtained from www.boud.com/sites/default/files/u27/boud_minerals_-_introduction_to_expancel_thermoplastic_microspheres.pdf.*

(Continued)

*Primary Examiner* — Patrick Niland
(74) *Attorney, Agent, or Firm* — Greenblum & Bernstein, P.L.C.

(57) ABSTRACT

The present invention relates to the field of heat sensitive optically variable inks and tamper indicating markings obtained thereof. The present invention relates to the field of irreversible changes in color and/or changes in structure upon a tampering attempt against articles or items comprising said tamper indicating markings through the use of temperature variation. In particular, the present invention provides optically variable ink compositions comprising a plurality of optically variable pigment particles and a plurality of thermally expandable spheres; tamper indicating marking comprising the optically variable ink compositions described herein; their uses as a proof of an illegal action as well as methods for detecting a tampering activity of a marking including the optically variable ink composition described herein.

24 Claims, 1 Drawing Sheet

(56) References Cited

FOREIGN PATENT DOCUMENTS

| | | |
|---|---|---|
| WO | 2004/072160 | 8/2004 |
| WO | 2006/063926 | 6/2006 |
| WO | 2007/131833 | 11/2007 |
| WO | 2007/142593 | 12/2007 |
| WO | 2008/083894 | 7/2008 |
| WO | WO 2013/049696 * | 4/2013 |

OTHER PUBLICATIONS

J.M. Adams et al., "Printing Technology, Delmar Thomson Learning $5^{th}$ edition", 2002, pp. 359-360.

* cited by examiner

HEAT SENSITIVE TAMPER INDICATING MARKINGS

CROSS-REFERENCE TO RELATED APPLICATIONS

This application claims the benefit of U.S. Provisional Application No. 61/834,201, filed Jun. 12, 2013, the disclosure of which is incorporated by reference herein in its entirety.

FIELD OF THE INVENTION

The present invention relates to the field of heat sensitive optically variable inks and tamper indicating markings obtained thereof. In particular, the present invention relates to the field of irreversible change in color and/or change in structure upon a tampering attempt against articles or items comprising said tamper indicating markings through the use of temperature variation.

BACKGROUND OF THE INVENTION

With the constantly improving quality of color photocopies and printings and in an attempt to protect high value documents and high value articles such as banknotes, identity documents and high value goods, it has been the conventional practice to incorporate various security elements in or on these documents or articles. Typical examples of security elements include security threads or stripes, windows, fibers, planchettes, foils, decals, holograms, watermarks, security inks or compositions comprising optically variable pigment particles, magnetic or magnetizable optically variable pigment particles, thermochromic pigment particles, photochromic pigment particles, luminescent, infrared-absorbing, ultraviolet-absorbing or magnetic compounds.

Nowadays, counterfeiting is a global problem which has an impact not only on manufacturers but also on the consumers and governments. Indeed, counterfeiting may also have an impact on government revenues in that it affects the collection of taxes for example for cigarettes and alcohols because of the existence of a black market where it is impossible to track and trace counterfeit (smuggled, diverted, etc.) products with no valid tax stamps.

Various solutions have been developed in the field of packaging or as a protection for items or goods and mainly used for high value documents or high value articles. Those solutions include the incorporation of tamper evident structures or void tamper security evident structures which include a proof of any alteration or manipulation of packaging or items or good that may have occurred.

For example, labels or items whose primary function is the security and prevention of counterfeiting or illegal reproduction of high value articles may be forcibly removed or detached with the fraudulent aim of re-using them on articles of lesser value. Typical examples of such fraudulent activities include the increase of temperature to be able to remove the labels or items intact and thereby allowing their re-use on other less valuable or fake articles. The need for security and for identification of any tampering that might have occurred involves many and diversified fields including without limitation the food and wine industry, the cosmetic industry, the pharmaceutical industry, the food processing industry, the electrical/electronic industry, tax stamps or banderols. To overcome those fraudulent activities, various solutions have been developed and include for example the incorporation of tamper evident structures or void tamper security evident structures which include a proof of any alteration or manipulation that may have occurred.

For example, temperature-indicating materials capable of changing their color tone upon exposure to a defined temperature have been used as means for detecting whether a particular product experienced or was exposed to a temperature exceeding a predetermined level or not. Examples of known temperature-indicating materials include heat-fusible substances and acid-base indicators, the temperature-indicating materials being reversible temperature indicators since they undergo color change upon heating and the color tone thereof returns back to the original one when they are cooled.

US 2013/0014690, which is incorporated by reference herein in its entirety, discloses a temperature management indicator which is capable of indicating specific temperature ranges by reversible color changes. The disclosed temperature management indicator comprises a reversible temperature indicating member including reversible temperature indicating pigment particles devoid of mercury, the pigment particles being dispersed in a resin. It is further disclosed that an additional irreversible temperature indicating member may be arranged on an indicator base plate, the irreversible temperature indicating member including a thermofusible substance-absorptive base material or a thermofusible substance-permeable material.

US 2001/0044014, which is incorporated by reference herein in its entirety, discloses an irreversible heat-sensitive composition comprising a mixture of a granular or powdery heat-fusible substance having a melting point corresponding to a temperature to be recorded and a granular or powdery dyestuff diffusible into the fused heat-fusible substance through dispersion or dissolution. A heat-sensitive indicator comprising a substrate provided thereon with the printed heat-sensitive ink is further disclosed.

Therefore, there remains a need for a solution combining high security against counterfeiting and illegal reproduction as well as avoiding fake, manipulation, alteration or diversion of goods, articles, items or packaging containing any valuable products.

SUMMARY OF THE INVENTION

Accordingly, it is an object of the present invention to provide optically variable ink compositions comprising a plurality of optically variable pigment particles and a plurality of thermally expandable spheres, preferably said plurality of optically variable pigment particles are selected from of the group consisting of thin film interference pigment particles, interference coated pigment particles, cholesteric liquid crystal pigment particles and mixtures thereof.

There are disclosed and claimed herein tamper indicating markings on a substrate or an article, said tamper indicating markings comprising the optically variable ink composition described herein, processes for manufacturing the tamper indicating markings described herein and tamper indicating markings obtained therefrom. The processes for manufacturing the tamper indicating markings described herein comprise applying on the substrate or the article, preferably by a printing process selected from the group consisting of screen printing, flexo printing and rotogravure, the optically variable ink composition described herein.

There are disclosed and claimed herein substrates or articles comprising the optically variable ink described herein or the tamper indicating marking described herein.

There are disclosed and claimed herein uses of the optically variable ink composition described herein or the tamper indicating marking described herein as a proof of an illegal action, preferably a tampering comprising an increase of temperature of at least 35° C. as well as uses of the plurality of thermally expandable spheres described herein in the optically variable ink composition comprising a plurality of optically pigment particles, preferably selected from the group consisting of thin film interference pigment particles, interference coated pigment particles, cholesteric liquid crystal pigment particles and mixtures thereof, describes herein as a tampering agent in case of an illegal action, preferably a tampering activity comprising an increase of temperature of at least 35° C.

There are disclosed and claimed herein methods for detecting, revealing or indicating an illegal action, preferably a tampering activity, against an article or item, said tampering activity comprising an increase of temperature of at least 35° C., wherein the method comprises adding the plurality of thermally expandable spheres described herein in the optically variable ink composition comprising a plurality of optically variable pigment particles preferably selected from the group consisting of thin film interference pigment particles, interference coated pigment particles, cholesteric liquid crystal pigment particles and mixtures thereof, described herein prior to applying said optically variable ink on said article or item.

There are disclosed and claimed herein methods for detecting tampering activity of a marking on a substrate, the tampering activity comprising an increase of temperature of at least 35° C. and the marking including the optically variable ink composition described herein, the methods comprising detecting an irreversible change in color and/or a change in structure of the marking.

On the contrary to the native or not tampered state wherein the tamper indicating marking exhibit colorshifting properties as an overt security feature, the forcibly heated tamper indicating marking exhibits an irreversible color fully inhibiting the observation of the colorshifting properties of the native tamper indicating marking. Indeed, upon interaction with heat the tamper indicating marking undergoes an irreversible change in color and/or change in structure. In addition to the permanent change in color and change in structure, the heated optically variable ink or tamper indicating marking exhibits a reduced adhesion to the substrate onto which it is applied. Therefore, the tamper indicating marking according to the present allows an easy detection of a fraudulent tampering activity and rendering a tampered marking inoperable. For example, an increase of temperature with the aim of forcibly removing the tamper indicating marking of the present invention would render its re-use on another less valuable document or article or fake article or document impossible without detection.

Due to the presence of the plurality of thermally expandable spheres described herein in optically variable inks applied as a tamper indicating marking on an article or item, any attempts of tampering against the article or item can be easily verified. Therefore, the present invention provides an efficient and highly secure solution combining a high level of security against counterfeiting and illegal reproduction with efficient and easy detection of temperature variation. Typically, any attempts of tampering against an article or item using a fraudulent increase of temperature includes or comprises a temperature increase of an increase of at least 35° C., at least 40° C., at least 45° C. or at least 50° C.

In addition to the evidence of tampering activity provided by the present invention, the present invention advantageously provides a solution to assess if a sensitive product such as for example a pharmaceutical article, a food product or an electrical/electronic article underwent an increase of temperature that may be detrimental for the safety of the customers.

BRIEF DESCRIPTION OF THE DRAWINGS

The present invention is further described in the detailed description which follows, in reference to the noted drawings by way of non-limiting examples of exemplary embodiments of the present invention, wherein.

DETAILED DESCRIPTION

Definitions

The following definitions are to be used to interpret the meaning of the terms discussed in the description and recited in the claims.

As used herein, the article "a" indicates one as well as more than one and does not necessarily limit its referent noun to the singular.

As used herein, the term "about" means that the amount or value in question may be the specific value designated or some other value in its neighborhood. Generally, the term "about" denoting a certain value is intended to denote a range within ±5% of the value. As one example, the phrase "about 100" denotes a range of 100±5, i.e. the range from 95 to 105. Preferably, the range denoted by the term "about" denotes a range within ±3% of the value, more preferably ±1%. Generally, when the term "about" is used, it can be expected that similar results or effects according to the invention can be obtained within a range of ±5% of the indicated value.

As used herein, the term "and/or" or "at least one" means that either all or only one of the elements of the group may be present. For example, "A and/or B" or "at least one of A and B" shall mean "only A, or only B, or both A and B". In the case of "only A", the term also covers the possibility that B is absent, i.e. "only A, but not B".

As used herein, the term "at least" is meant to define one or more than one, for example one or two or three.

The term "comprising" as used herein is intended to be non-exclusive and open-ended. Thus, for instance a composition comprising a compound A may include other compounds besides A.

The term "tampering" means an unauthorized interference with a substrate, article or item whether for the purpose of forgery or substitution.

Optically variable elements (also referred in the art as colorshifting or goniochromatic elements) exhibit a viewing-angle or incidence-angle dependent color, and are used to protect high value documents or articles against counterfeiting and/or illegal reproduction by commonly available color scanning, printing and copying office equipment. For example, coatings or layers comprising optically variable pigment particles exhibits a colorshift upon variation of the viewing angle (e.g., from a viewing angle of about 90° with respect to the plane of the coating or layer to a viewing angle of about 22.5° with respect to the plane of the coating or layer) from a color impression CI1 (e.g., green) to a color impression CI2 (e.g., blue). In addition to the overt security provided by the colorshifting property of the optically variable pigment particles, which allows an easy detection, recognition and/or discrimination of the high value documents or articles from their possible counterfeits with the unaided human senses, the colorshifting property of the optically variable pigment particles may be used as a machine readable tool for the recognition of the high value documents or articles. Thus, the colorshifting properties of the optically variable pigment particles may simultaneously be used as a covert or semi-covert security feature in an authentication process wherein the optical (e.g., spectral) properties of the pigment particles are analyzed.

The optically variable ink composition according to the present invention comprises a plurality of optically variable pigment particles. Preferably, the plurality of optically variable pigment particles are selected from of the group consisting of thin film interference pigment particles, interference coated pigment particles, cholesteric liquid crystal pigment particles and mixtures thereof. The optically variable pigment particles are preferably present in an amount from about 10 wt-% to about 40 wt-%, and more preferably from about 12 wt-% and about 35 wt-%, the weight percents being based on the total weight of the optically variable ink composition.

Suitable thin-film interference pigment particles exhibiting optically variable characteristics are known to those skilled in the art and disclosed in, for example, U.S. Pat. No. 4,705,300; U.S. Pat. No. 4,705,356; U.S. Pat. No. 4,721,271; U.S. Pat. No. 5,084,351; U.S. Pat. No. 5,214,530; U.S. Pat. No. 5,281,480; U.S. Pat. No. 5,383,995; U.S. Pat. No. 5,569,535, U.S. Pat. No. 5,571,624, each of which is incorporated by reference herein in its entirety, and in documents related to these. When at least a part of the of optically variable pigment particles is constituted by thin film interference pigment particles, it is preferred that the thin film interference pigment particles comprise a Fabry-Perot reflector/dielectric/absorber multilayer structure and more preferably a Fabry-Perot absorber/dielectric/reflector/dielectric/absorber multilayer structure, wherein the absorber layers are partially transmitting and partially reflecting, the dielectric layers are transmitting and the reflective layer is reflecting the incoming light. Preferably, the reflector layer is selected from of the group consisting of metals, metal alloys and combinations thereof, preferably selected from the group consisting of reflective metals, reflective metal alloys and combinations thereof and more preferably selected from the group consisting of aluminum (Al), chromium (Cr), nickel (Ni), and mixtures thereof and still more preferably aluminum (Al). Preferably, the dielectric layers are independently selected from the group consisting of magnesium fluoride ($MgF_2$), silicium dioxide ($SiO_2$) and mixtures thereof and more preferably magnesium fluoride ($MgF_2$). Preferably, the absorber layers are independently selected from the group consisting of chromium (Cr), nickel (Ni), metallic alloys and mixtures thereof and more preferably chromium (Cr). When at least a part of the optically variable pigment particles is constituted by thin film interference pigment particles, it is particularly preferred that the thin film interference pigment particles comprise a Fabry-Perot absorber/dielectric/reflector/dielectric/absorber multilayer structure comprising a $Cr/MgF_2/Al/MgF_2/Cr$ multilayer structure.

Liquid crystals in the cholesteric phase exhibit a molecular order in the form of a helical superstructure perpendicular to the longitudinal axes of its molecules. The helical superstructure is at the origin of a periodic refractive index modulation throughout the liquid crystal material, which in turn results in a selective transmission/reflection of determined wavelengths of light (interference filter effect). Cholesteric liquid crystal polymers can be obtained by subjecting one or more crosslinkable substances (nematic compounds) with a chiral phase to alignment and orientation. The particular situation of the helical molecular arrangement leads to cholesteric liquid crystal materials exhibiting the property of reflecting a circularly polarized light component within a determined wavelength range. The pitch (i.e., the distance over which a full rotation of 360° of the helical arrangement is completed) can be tuned in particular by varying selectable factors including the temperature and solvents concentration, by changing the nature of the chiral component(s) and the ratio of nematic and chiral compounds. Crosslinking under the influence of UV radiation freezes the pitch in a predetermined state by fixing the desired helical form so that the color of the resulting cholesteric liquid crystal materials is no longer depending on external factors such as the temperature. Cholesteric liquid crystal materials may then be shaped to cholesteric liquid crystal pigment particles by subsequently comminuting the polymer to the desired pigment particle size. Examples of films and pigment particles made from cholesteric liquid crystal materials and their preparation are disclosed in U.S. Pat. No. 5,211,877; U.S. Pat. No. 5,362,315 and U.S. Pat. No. 6,423,246 and in EP 1 213 338 B1; EP 1 046 692 B1 and EP 0 601 483 B1, which are incorporated by reference herein in their entireties. Should the circular polarized light reflection be used as a covert security element requiring an authentication tool to be verified and since the human eye is unable to detect the polarization state of the light it is receiving, such as the circular polarization effect of cholesteric liquid crystal pigment particles, a device, such as for example a light-polarizing filter is required for the detection of said polarization state. Typically, the viewing equipment comprises a pair of circularly polarized filters, a left circular polarized filter and a right circular polarized filter.

Suitable interference coated pigment particles include, without limitation, structures comprising a substrate selected from the group consisting of metallic cores, such as titanium, silver, aluminum, copper, chromium, iron, germanium, molybdenum, tantalum or nickel coated with one or more layers made of metal oxides as well as structure comprising a core made of synthetic or natural micas, other layered silicates (e.g., talc, kaolin and sericite), glasses (e.g., borosilicates), silicium dioxides ($SiO_2$), aluminum oxides ($Al_2O_3$), titanium oxides ($TiO_2$), graphites and mixtures thereof coated with one or more layers made of metal oxides (e.g. titanium oxides, zirconium oxides, tin oxides, chromium oxides, nickel oxides, copper oxides and iron oxides). The structures described hereabove have been described for example in Chem. Rev. 99 (1999), G. Pfaff and P. Reynders, pages 1963-1981 and WO 2008/083894 A2, which are incorporated by reference herein in their entireties. Typical examples of these interference coated pigment particles include without limitation silicium oxide cores coated with one or more layers made of titanium oxide, tin oxide and/or iron oxide; natural or synthetic mica cores coated with one or more layers made of titanium oxide, silicium oxide and/or iron oxide, in particular mica cores coated with alternate layers made of silicium oxide and titanium oxide; borosilicate cores coated with one or more layers made of titanium oxide, silicium oxide and/or tin oxide; and titanium oxide cores coated with one or more layers made of iron oxide, iron oxide-hydroxide, chromium oxide, copper oxide, cerium oxide, aluminum oxide, silicium oxide, bismuth vanadate, nickel titanate, cobalt titanate and/or antimony-doped, fluorine-doped or indium-doped tin oxide; aluminum oxide cores coated with one or more layers made of titanium oxide and/or iron oxide.

According to one embodiment of the present invention, at least a part of the plurality of optically variable pigment particles is constituted by optically variable magnetic or magnetizable pigment particles. These can more preferably be selected from the group consisting of magnetic thin-film interference pigment particles, magnetic cholesteric liquid crystal pigment particles and mixtures thereof. Due to their magnetic characteristics being machine readable, optically variable ink compositions comprising optically variable magnetic or magnetizable pigment particles may be detected for example with the use of specific magnetic detectors. Therefore, optically variable ink compositions comprising optically variable magnetic or magnetizable pigment particles may be used as a covert or semi-covert security element (those requiring an authentication tool to be verified) for any article or item comprising said ink compositions.

Suitable magnetic thin film interference pigment particles exhibiting optically variable characteristics are known to those skilled in the art and disclosed in U.S. Pat. No. 4,838,648; WO 2002/073250 A2; EP 686 675 B1; WO 2003/00801 A2; U.S. Pat. No. 6,838,166; WO 2007/131833 A1 which are incorporated by reference herein in their entireties, and in the documents related thereto. Preferably, the optically variable magnetic or magnetizable pigment particles are magnetic thin film interference pigment particles comprising pigment particles having a five-layer Fabry-Perot multilayer structure and/or pigment particles having a six-layer Fabry-Perot multilayer structure and/or pigment particles having a seven-layer Fabry-Perot multilayer structure. Preferred five-layer Fabry-Perot multilayer structures include absorber/dielectric/reflector/dielectric/absorber multilayer structures wherein the reflector and/or the absorber is also a magnetic layer. Preferred six-layer Fabry-Perot multilayer structures include absorber/dielectric/reflector/magnetic/dielectric/absorber multilayer structures, the multilayer structure preferably comprising Cr/MgF$_2$/Al/magnetic/MgF$_2$/Cr multilayer structures. Preferred seven-layer Fabry Perot multilayer structures comprise absorber/dielectric/reflector/magnetic/reflector/dielectric/absorber multilayer structures, such as disclosed in U.S. Pat. No. 4,838,648, which is incorporated by reference herein in its entirety; and more preferably seven-layer Fabry-Perot absorber/dielectric/reflector/magnetic/reflector/dielectric/absorber multilayer structures. Preferably, the reflector layers described herein are selected from the group consisting of metals, metal alloys and combinations thereof, preferably selected from the group consisting of reflective metals, reflective metal alloys and combinations thereof, and more preferably from the group consisting of aluminum (Al), chromium (Cr), nickel (Ni), and mixtures thereof, and still more preferably aluminum (Al). Preferably, the dielectric layers are independently selected from the group consisting of magnesium fluoride (MgF$_2$), silicium dioxide (SiO$_2$) and mixtures thereof, and more preferably magnesium fluoride (MgF$_2$). Preferably, the absorber layers are independently selected from the group consisting of chromium (Cr), nickel (Ni), metallic alloys and mixtures thereof. Preferably, the magnetic layer is selected from the group consisting of nickel (Ni), iron (Fe) and cobalt (Co), alloys comprising nickel (Ni), iron (Fe) and/or cobalt (Co), and mixtures thereof. It is particularly preferred that the magnetic thin film interference pigment particles comprise a seven-layer Fabry-Perot absorber/dielectric/reflector/magnetic/reflector/dielectric/absorber multilayer structure of a Cr/MgF$_2$/Al/Ni/Al/MgF$_2$/Cr multilayer structure. Magnetic thin film interference pigment particles described herein are typically manufactured by vacuum deposition of the different required layers onto a web. After deposition of the desired number of layers, e.g., by PVD, the stack of layers is removed from the web, either by dissolving a release layer in a suitable solvent, or by stripping the material from the web. The so-obtained material is then broken down to flakes which have to be further processed by grinding, milling or any suitable method. The resulting product comprises flat flakes with broken edges, irregular shapes and different aspect ratios. Further information on the preparation of suitable magnetic thin film interference pigment particles can be found e.g., in EP 1 710 756 A1, which is incorporated by reference herein in its entirety. Preferred magnetic thin film interference pigment particles exhibiting optically variable characteristics for the present invention are flakes having a diameter from about 2 microns to about 50 microns, preferably from about 3 microns to about 50 microns.

Suitable magnetic cholesteric liquid crystal pigment particles exhibiting optically variable characteristics include without limitation monolayered cholesteric liquid crystal pigment particles and multilayered cholesteric liquid crystal pigment particles and are disclosed, for example, in WO 2006/063926 A1, U.S. Pat. No. 6,582,781 and U.S. Pat. No. 6,531,221, which are incorporated by reference herein in their entireties. WO 2006/063926 A1 discloses monolayers and pigment particles obtained therefrom with high brilliance and colorshifting properties with additional particular properties such as magnetizability. The disclosed monolayers and pigment particles obtained therefrom by comminuting the monolayers comprise a three-dimensionally cross-linked cholesteric liquid crystal mixture and magnetic nanopigment particles. U.S. Pat. No. 6,582,781 and U.S. Pat. No. 6,410,130 disclose platelet-shaped cholesteric multilayer pigment particles which comprise the sequence $A^1$/B/$A^2$, wherein $A^1$ and $A^2$ may be identical or different and each comprises at least one cholesteric layer, and B is an interlayer absorbing all or some of the light transmitted by the layers $A^1$ and $A^2$ and imparting magnetic properties to said interlayer. U.S. Pat. No. 6,531,221 discloses platelet-shaped cholesteric multilayer pigment which comprise the sequence A/B and if desired C, wherein A and C are absorbing layers comprising pigment particles imparting magnetic properties, and B is a cholesteric layer.

Suitable interference coated pigment particles comprising a magnetic material include the interference coated pigment particles described hereabove, wherein the pigment comprise a magnetic material.

The optically variable ink compositions described herein are preferably thermal drying compositions, and are more preferably selected from the group consisting of solvent-borne compositions, waterborne compositions and mixtures thereof. Moreover, the optically variable ink compositions do not include UV curable optically variable ink compositions.

Thermal drying compositions include compositions of any type of aqueous compositions or solvent-based compositions which are dried by hot air, infrared or by a combination of hot air and infrared. Typical examples of thermal drying compositions comprises components including without limitation resins, such as polyester resins, polyether resins, vinyl chloride polymers and vinyl chloride based copolymers, nitrocellulose resins, cellulose acetobutyrate or acetopropionate resins, maleic resins, polyamides, polyolefins, polyurethane resins, functionalized polyurethane resins (e.g., carboxylated polyurethane resins), polyurethane alkyd resins, polyurethane-(meth)acrylate resins, urethane-(meth) acrylic resins, styrene (meth)acrylate resins or mixtures thereof. The term "(meth)acrylate" or "(meth)acrylic" in the context of the present invention refers to the acrylate as well as the corresponding methacrylate or refers to the acrylic as well as the corresponding methacrylic. As used herein, the term "solvent-borne compositions" refers to compositions whose liquid medium or carrier substantially comprise one or more organic solvents, provided that the one or more organic solvents do not interfere with the thermally expandable spheres or are not detrimental to the thermally expandable spheres. Examples of such solvents include without limitation alcohols (such as for example methanol, ethanol, isopropanol, n-propanol, ethoxy propanol, n-butanol, sec-butanol, tert-butanol, iso-butanol, 2-ethylhexyl-alcohol and mixtures thereof); polyols (such as for example glycerol, 1,5-pentanediol, 1,2,6-hexanetriol and mixtures thereof); esters (such as for example ethyl acetate, n-propyl acetate, n-butyl acetate and mixtures thereof); carbonates (such as for example dimethyl carbonate, diethylcarbonate, di-n-butylcarbonate, 1,2-ethylencarbonate, 1,2-propylenecarbonate, 1,3-propylencarbonate and mixtures thereof); aromatic solvents (such as for example toluene, xylene and mixtures thereof); ketones and ketone alcohols (such as for example acetone, methyl ethyl ketone, methyl isobutyl ketone, cyclohexanone, diacetone alcohol and mixtures thereof); amides (such as for example dimethylformamide, dimethyl-acetamide and mixtures thereof); aliphatic or cycloaliphatic hydrocarbons; chlorinated hydrocarbons (such as for example dichloromethane); nitrogen-containing heterocyclic compound (such as for example N-methyl-2-pyrrolidone, 1,3-dimethyl-2-imidazolidone and mixtures thereof); ethers (such as for example diethyl ether, tetrahydrofuran, dioxane and mixtures thereof); alkyl ethers of a polyhydric alcohol (such as for example 2-methoxyethanol, 1-methoxypropan-2-ol and mixtures thereof); alkylene glycols, alkylene thioglycols, polyalkylene glycols or polyalkylene thioglycols (such for example ethylene glycol, polyethylene glycol (such as for example diethylene glycol, triethylene glycol, tetraethylene glycol), propylene glycol, polypropylene glycol (such as for example dipropylene glycol, tripropylene glycol), butylene glycol, thiodiglycol, hexylene glycol and mixtures thereof); nitriles (such as for example acetonitrile, propionitrile and mixtures thereof), and sulfur-containing compounds (such as for example dimethylsulfoxide, sulfolan and mixtures thereof). Preferably, the one or more organic solvents are selected from the group consisting of alcohols, esters and mixtures thereof.

The thermally expandable spheres described herein preferably comprise a polymer shell, preferably a thermoplastic polymer, encapsulating a propellant. Under the influence of heat such as for example a temperature of at least 35° C., at least 40° C., at least 45° C. or at least 50° C., the shell of the thermally expandable spheres softens and the pressure within the spheres strongly increases, thus resulting in a dramatic increase of the volume and expansion of the spheres.

The plurality of thermally expandable spheres described herein are preferably present in an a mount from about 5 wt-% and 20 wt-%, preferably from about 8 wt-% to 15 wt-%, in the optically variable inks described herein, the weight percents being based on the total weight of the optically variable ink composition. The thermally expandable spheres described herein are particularly suitable as a tampering agent in optically variable inks comprising the plurality of optically variable pigment particles described herein in case of an illegal action, in particular in case of a fraudulent increase of temperature. Typically and as mentioned hereabove, a fraudulent increase of temperature includes an increase of at least 35° C., at least 40° C., at least 45° C. or at least 50° C.

Preferably, the polymer shell of the thermally expandable spheres described herein is a thermoplastic polymer shell made of one or more homo- or co-polymers obtained by polymerizing ethylenically unsaturated monomers, as well as mixtures thereof. Those monomers include without limitation nitrile containing monomers such as acrylonitrile, methacrylonitrile, α-chloroacrylonitrile, α-ethoxyacrylonitrile, fumaronitrile or crotonitrile; (meth)acrylic esters such as methyl (meth)acrylate or ethyl (meth)acrylate; vinyl halides such as vinyl chloride; vinyl esters such as vinyl acetate other vinyl monomers such as vinyl pyridine; vinylidene halides such as vinylidene chloride; styrenes such as styrene, halogenated styrenes or α-methyl styrene; and dienes such as butadiene, isoprene and chloroprene. The term "(meth)acrylate" or "(meth)acrylic" in the context of the present invention refers to the acrylate as well as the corresponding methacrylate or refers to the acrylic as well as the corresponding methacrylic. Any mixtures of the above mentioned monomers may also be used. According to one embodiment, the monomers comprise at least one methyl acrylate monomer. According to another embodiment, the monomers comprise at least one vinylidene halide monomer, more preferably at least one vinylidene chloride monomer. According to one embodiment, the monomers comprise at least one nitrile containing monomer, preferably at least one of acrylonitrile monomer According to one embodiment, the monomers comprise at least one vinylidene halide, preferably at least one vinylidene chloride monomer, and at least one nitrile containing monomer, preferably at least one of acrylonitrile monomer. According to one embodiment, the monomers comprise at least one (meth)acrylic ester monomer, preferably at least one (meth)acrylic ester monomer such as methyl (meth)acrylate. According to one embodiment, the thermoplastic polymer shell is made of a co-polymer obtained by polymerizing at least one acrylonitrile monomer, at least one vinylidene chloride monomer and optionally at least one methyl (meth)acrylate monomer.

The propellant encapsulated by the polymer shell described herein is a material having a boiling temperature not higher than the softening temperature of the polymer shell. Preferably, the propellant comprises one or more hydrocarbons; preferably the one or more hydrocarbons are selected from the group consisting of propane, n-pentane, isopentane, neopentane, butane, isobutane, hexane, isohexane, neohexane, heptane, isoheptane, octane, isooctane and mixtures thereof. Aside from those disclosed one or more hydrocarbons, other hydrocarbon types can also be used, such as petroleum ether, or chlorinated or fluorinated hydrocarbons, such as methyl chloride, methylene chloride, dichloroethane, dichloroethylene, trichloroethane, trichloroethylene, trichlorofluoromethane, perfluorinated hydrocarbons, etc. Preferred propellants comprise isobutane, alone or in a mixture with one or more other hydrocarbons.

The thermally expandable spheres described herein may be prepared by polymerizing the monomers in the presence of the propellant with the same methods as described in the earlier mentioned U.S. Pat. Nos. 3,615,972, 3,945,956, 5,536,756, 6,235,800, 6,235,394 and 6,509,384, and in EP 486080 A2, which are incorporated by reference herein in their entireties. Typical examples of those thermally expandable spheres are provided in U.S. Pat. Nos. 3,615,972; 4,287,308; 5,536,75; 6,509,384; 2006/0102307; WO 2007/142593 A1 and WO 2004/072160 A1, which are incorporated by reference herein in their entireties.

The thermally expandable spheres preferably have a pigment particle size from about 8 μm to about 40 μM, the pigment particle size D(0.5) referring to the average diameter of the dry unexpanded spheres. The pigment particle size of the thermally expandable spheres may be measured according to the method described in Technical Bulletin No. 3 "Pigment particle size of Expancel® Microspheres" as referenced in the Expancel® Product Specification (Issue 2011.11), issued by Akzo Nobel, which is incorporated by reference herein in its entirety. Under the influence of heat, the thermally expandable spheres may exhibit an increase of volume up to about 40 times.

Suitable thermally expandable spheres are available as Expancel® Akzo Nobel.

Under the influence of heat such as for example a temperature of at least 35° C., at least 40° C., at least 45° C. or at least 50° C., the optically variable ink described herein or the tamper indicating marking described herein exhibits a permanent and irreversible change in color and/or change in structure. Advantageously, the permanent and irreversible change in color and/or change in structure may be used as a proof of a tampering activity comprising a temperature increase of at least 35° C., at least 40° C., at least 45° C. or at least 50° C.

The optically variable compositions described herein may further comprise one or more machine readable materials. When present, the one or more machine readable materials are preferably selected from the group consisting of magnetic materials, luminescent materials, electrically conductive materials, infrared-absorbing materials and mixtures thereof. As used herein, the term "machine readable material" refers to a material which exhibits at least one distinctive property which is detectable by a device or machine, such as for example a magnetic detector (when the machine readable security material is a material having magnetic properties) an IR-camera (when the machine readable security material is a material having IR-absorbing properties), or a circularly polarizing filter (when the machine readable security material is a material having light polarization properties), and which can be comprised in a marking so as to confer a way to authenticate the marking or article comprising the marking by the use of a particular equipment for its authentication. The optically variable compositions described herein may further comprise one or more marker substances and/or taggants.

The optically variable compositions described herein may further comprise one or more additives including without limitation compounds and materials which are used for adjusting physical, rheological and chemical parameters of the composition such as the viscosity (e.g., solvents and surfactants), the consistency (e.g., anti-settling agents, fillers and plasticizers), the foaming properties (e.g., antifoaming agents), the lubricating properties (waxes), UV stability (photostabilizers) and adhesion properties, etc. Additives described herein may be present in the optically variable compositions described herein in amounts and in forms known in the art, including in the form of so-called nanomaterials where at least one of the dimensions of the pigment particles is in the range of 1 to 1000 nm.

The optically variable compositions described herein may be prepared by dispersing or mixing the plurality of optically variable pigment particles described herein and the one or more additives when present in the presence of the binder or binder precursors described herein, thus forming liquid or pasty inks. While the thermally expandable spheres may then be added to the so-obtained inks either in a dry form or in a water-based or solvent based system, preferably, the thermally expandable spheres are then added to the so-obtained inks in their unexpanded dry form.

The present invention further provides tamper indicating markings on a substrate or an article, the tamper indicating marking comprising the optically variable ink composition described herein. The tamper indicating marking is preferably in the form of indicia, wherein the term "indicia" refers to a layer such as a pattern including without limitation symbols, alphanumeric symbols, motifs, letters, words, numbers, logos and drawings.

According to one embodiment, the tamper indicating markings described herein are present on a substrate. Preferably, the substrate described herein is selected from the group consisting of fibrous materials (e.g. cellulose), paper-containing materials, plastics and polymers, composite materials, metals, metalized materials, glasses, ceramics and combinations thereof. Typical examples of plastic or polymer substrates are substrates made of polypropylene (PP), polyethylene (PE), polycarbonate (PC), polyvinyl chloride (PVC) and polyethylene terephthalate (PET). Typical examples of composite materials include without limitation multilayer structures or laminates of paper and at least one plastic or polymer material such as those described hereabove as well as plastic and/or polymer fibers incorporated in a paper-like or fibrous material such as those described hereabove. The substrate described herein onto which the tamper indicating marking is applied may be an intrinsic part of an article or item, or alternatively, may be an auxiliary substrate such as for example a seal, label, foil or decal which is subsequently transferred to another article or item. Still alternatively, the substrate described herein onto which the tamper indicating marking is applied may be an auxiliary substrate such as for example a can, capsule, cork, packaging, cartridge for holding various high values items such as, e.g., cosmetic articles, nutraceutical articles, pharmaceutical articles, alcohols, beverages or foodstuffs, electrical/electronics articles, fabrics, jewelry or cigarettes. According to another embodiment, the tamper indicating markings described herein are directly present on an article or item, preferably a high value document or a high value article. Typical examples of high value documents include without limitation tax stamps, tax labels or banderols. Typical example of high value articles include without limitation cosmetic articles, nutraceutical articles, pharmaceutical articles, alcohols, beverages or foodstuffs, electrical/electronics articles, fabrics or jewelry. It is pointed out that the disclosed substrates, high value documents and high value articles are given exclusively for exemplifying purposes, without restricting the scope of the invention.

Figure 1:
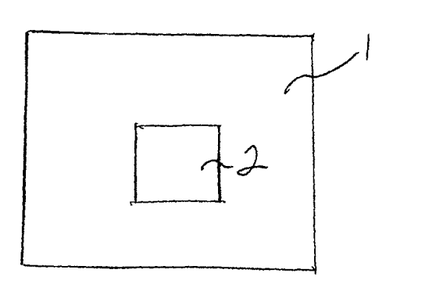
FIG. 1 illustrates a substrate including a tamper indicating marking according to one non-limiting embodiment.

Also described herein are substrates or articles comprising the optically variable ink described herein or the tamper indicating marking described herein. For example, FIG. 1 generally illustrates a substrate 1 including a tamper indicating marking 2 associated therewith. Each of the substrate and the tamper indicating marking can be of any size and shape, including partial or complete overlap with each other.

Should the adhesion between the tamper indicating marking described herein and the substrate described herein or the article described herein be insufficient, for example, due to the substrate or article material, a surface unevenness or a surface inhomogeneity, one or more additional layers, coatings or primers between the substrate or the article and the tamper indicating marking might be applied as known for those skilled in the art, provided that they do not interfere with the tamper indicating marking.

Also described herein are processes for manufacturing the tamper indicating marking described herein and tamper indicating markings obtained therefrom. The tamper indicating markings described herein are manufactured by a process comprising applying on the substrate or article described herein, preferably by a printing process selected from the group consisting of screen printing, flexo printing and rotogravure, the optically variable ink composition described herein. These processes are well-known to the skilled man and are described for example in Printing Technology, J. M. Adams and P. A. Dolin, Delmar Thomson Learning, $5^{th}$ Edition, 2002, which is incorporated by reference herein in its entirety. Subsequently to the application step, the optically variable ink composition described herein is dried, preferably by hot air, infrared or by a combination of hot air and infrared.

As known by those skilled in the art, the term rotogravure refers to a printing process which is described for example in "Handbook of print media", Helmut Kipphan, Springer Edition, page 48, which is incorporated by reference herein in its entirety. Rotogravure is a printing process wherein the image elements are engraved into the surface of a cylinder. The non-image areas are at a constant original level. Prior to printing, the entire printing plate (non-printing and printing elements) is inked with a composition and flooded with the composition. The composition is removed from the non-image by a wiper or a blade before printing, so that composition remains only in the cells. When the substrate to be printed travels between the cylinder and a rubber impression roller (hereafter referred as impression roller), it acts like a blotter and absorbs the remaining composition in the cells. The image is transferred from the cells to the substrate by a pressure typically in the range of 1 to 4 bars and by the adhesive forces between the substrate and the ink. The term rotogravure does not encompass intaglio printing processes (also referred in the art as engraved steel die or copper plate printing processes) which rely for example on a different type of ink.

Flexography preferably uses a unit with a doctor blade, preferably a chambered doctor blade, an anilox roller and plate cylinder. The anilox roller advantageously has small cells whose volume and/or density determines the composition application rate. The doctor blade lies against the anilox roller, and scraps off surplus composition at the same time. The anilox roller transfers the composition to the plate cylinder which finally transfers the composition to the substrate. Specific design might be achieved using a designed photopolymer plate. Plate cylinders can be made from polymeric or elastomeric materials. Polymers are mainly used as photopolymer in plates and sometimes as a seamless coating on a sleeve. Photopolymer plates are made from light-sensitive polymers that are hardened by ultraviolet (UV) light. Photopolymer plates are cut to the required size and placed in an UV light exposure unit. One side of the plate is completely exposed to UV light to harden or cure the base of the plate. The plate is then turned over, a negative of the job is mounted over the uncured side and the plate is further exposed to UV light. This hardens the plate in the image areas. The plate is then processed to remove the unhardened photopolymer from the nonimage areas, which lowers the plate surface in these nonimage areas. After processing, the plate is dried and given a post-exposure dose of UV light to cure the whole plate. Preparation of plate cylinders for flexography is described in Printing Technology, J. M. Adams and P. A. Dolin, Delmar Thomson Learning, 5th Edition, pages 359-360, 2002, which is incorporated by reference herein in its entirety.

Screen printing (also referred in the art as silkscreen printing) is a stencil process whereby a composition is transferred to a surface through a stencil supported by a fine fabric mesh of silk, synthetic fibers or metal threads stretched tightly on a frame. The pores of the mesh are blocked-up in the non-image areas and left open in the image area, the image carrier being called the screen. During printing, the frame is supplied with the composition which is flooded over the screen and a urging means such as for example a squeegee is then drawn across it, thus forcing the composition through the open pores of the screen. At the same time, the surface to be printed is held in contact with the screen and the ink is transferred to it. Preferably a rotary screen cylinder is used. Screen printing is further described for example in The Printing ink manual, R. H. Leach and R. J. Pierce, Springer Edition, $5^{th}$ Edition, pages 58-62, 1993 (reprinted in 2004), which is incorporated by reference herein in its entirety and in Printing Technology, J. M. Adams and P. A. Dolin, Delmar Thomson Learning, $5^{th}$ Edition, pages 293-328, 2002, which is incorporated by reference herein in its entirety.

Also described herein are uses of the optically variable ink composition described herein or the tamper indicating marking described herein as a proof of an illegal action, in particular a tampering activity comprising a temperature increase of at least 35° C., at least 40° C., at least 45° C. or at least 50° C.

Subsequently to the application, preferably by a printing process selected from the group consisting of screen printing, flexo printing and rotogravure, of the optically variable ink described herein, the optically variable ink is preferably dried by a thermal process, provided that the thermal process does not interfere with the thermally expandable spheres. As mentioned hereabove, typical thermal processes use hot air, infrared or a combination of hot air and infrared.

Also described herein are uses of the plurality of thermally expandable spheres described herein in an optically variable ink composition comprising the plurality of optically variable pigment particles described herein as a tampering agent in case of an illegal action, in particular a tampering activity comprising a temperature increase of at least 35° C., at least 40° C., at least 45° C. or at least 50° C.

Also described herein are methods for detecting, revealing or indicating an illegal action, in particular a tampering activity, against an article or item, the tampering activity comprising an increase of temperature of at least 35° C., at least 40° C., at least 45° C. or at least 50° C., wherein the method comprises adding the plurality of thermally expandable spheres described herein in an optically variable ink composition comprising the plurality of optically variable pigment particles described herein prior to applying the optically variable ink on the article or item.

Also described herein are methods for detecting tampering activity of a marking on a substrate such as those described herein, the tampering activity comprising an increase of temperature of at least 35° C., at least 40° C., at least 45° C. or at least 50° C. and the marking including the optically variable ink composition described herein, the method comprising detecting an irreversible change in color and/or a change in structure of the marking. In particular, the irreversible change in color and/or the change in structure comprises the optically variable ink composition losing a color shifting property and/or a reduction in adhesion to the substrate. As mentioned hereabove, the marking on the substrate described herein may be associated with an article, said article being preferably a high value document selected from any one of tax stamps, tax labels and banderols, or any one of a high value article selected from cosmetic articles, nutraceutical articles, pharmaceutical articles, alcohols, beverages or foodstuffs, electrical/electronics articles, fabrics and jewelry.

EXAMPLES

The present invention is now described in greater detail with respect to non-limiting examples.

TABLE 1

Solvent-borne optically variable ink for screen printing.

| Ingredients | wt-% |
|---|---|
| Hydroxylated vinyl chloride resin | 10.6 |
| Mixture of two types of cholesteric liquid crystal pigment particles | 18 |
| Gellifying Additive | 2.1 |
| Anti-foaming Agent | 1.1 |
| Wax | 0.5 |
| Surfactant | 0.2 |
| Glycol Ester Solvent | 57.4 |
| Water | 0.1 |
| Thermally expandable spheres (sold as Expancel® 031DU40 by Akzo Nobel) | 10.0 |

TABLE 2

Water-borne optically variable ink for screen printing.

| Ingredients | wt-% |
|---|---|
| Acrylic Polymer | 52.7 |
| Water | 5.0 |
| Defoamer | 5.0 |
| Surfactant | 1.3 |
| Propylene Glycol | 6.0 |
| Mixture of two types of cholesteric liquid crystal pigment particles | 20 |
| Thermally expandable spheres (sold as Expancel® 031DU40 by Akzo Nobel) | 10.0 |

The wt-% are based on the total weight of the optically variable ink.

100 g of each of the optically variable ink of Tables 1 and 2 were prepared by mixing the ingredients described in Tables 1 and 2 except the thermally expandable spheres and the optically variable pigment particles. Mixing at room temperature was done with a dispersing propeller (stainless steel 5 cm diameter) at a speed of about 1500 rpm for a period of about 10 minutes. The optically variable pigment particles and thermally expandable spheres were then added to the so-obtained mixtures and mixing was done at a speed of 1500 rpm for a period of about 10 minutes.

Each of the optically variable inks of Tables 1 and 2 were applied by screen printing with specification of 230 mesh and 30° angle on a polylaminate layered substrate between 60-140 microns thick in the form of a circle so as to form a tamper indicating marking exhibiting a pink to green colorshifting property. Hardening was performed with hot air (heat gun) at about 60° C. for 3-4 seconds.

An attempt of tampering of the so-obtained tamper indicating markings was simulated by applying a temperature of about 90° C. by using a heat gun (Master ProHeat LCD, Dial-in Heat Gun Model PH1400), i.e. a temperature that is high enough to be used to remove the tamper indicating marking from an article or item and re-use said marking on a less valuable article or item. Upon exposure to heat, the tamper indicating markings exhibited a permanent and irreversible white color and a change in structural appearance and a reduced adhesion in comparison with the non-heated markings. Such irreversible color and structure changes may therefore be used as a proof of tampering activity comprising a temperature increase.

What is claimed is:

1. A tamper indicating marking on a substrate comprising an optically variable ink composition comprising optically variable pigment particles and thermally expandable spheres configured to provide a marking having an irreversible change in color and/or a loss of color shifting property upon expansion of the thermally expandable spheres when the marking is subjected to a temperature increase of at least 35° C.

2. The tamper indicating marking on a substrate according to claim 1, wherein the optically variable pigment particles are present in an amount from about 10 wt-% to about 40 wt-% and/or the thermally expandable spheres is present in an amount from about 5 wt-% and 20 wt-%, the weight percents being based on the total weight of the optically variable ink composition.

3. The tamper indicating marking on a substrate according to claim 1, wherein the thermally expandable spheres have a particle size from about 8 µm to about 40 µm.

4. The tamper indicating marking on a substrate according to claim 1, wherein the substrate is selected from the group consisting of fibrous materials, paper-containing materials, plastics and polymers, composite materials, metals, metalized materials, glasses, ceramics and combinations thereof.

5. A substrate or article comprising a tamper indicating marking comprising an optically variable ink comprising optically variable pigment particles and thermally expandable spheres configured to provide a marking having an irreversible change in color and/or a loss of color shifting property upon expansion of the thermally expandable spheres when subject to a temperature increase of at least 35° C.

6. The substrate or article comprising a tamper indicating marking according to claim 5, wherein the substrate or article comprises and article, and the article is a high value document selected from the group consisting of tax stamps, tax labels and banderols or a high value article selected from the group consisting of cosmetic articles, nutraceutical articles, pharmaceutical articles, alcohols, beverages or foodstuffs, electrical/electronics articles, fabrics and jewelry.

7. A process for manufacturing the substrate or article comprising a tamper indicating marking recited in claim 5, the process comprising applying on the substrate or the article, the optically variable ink composition comprising optically variable pigment particles and thermally expandable spheres configured to provide a marking having an irreversible change in color and/or a loss of color shifting property upon expansion of the thermally expandable spheres when subjected to a temperature increase of at least 35° C.

8. A method for marking an article or item for detecting, revealing or indicating an illegal action against an article or item, the illegal action comprising an increase of temperature of at least 35° C., wherein the method comprises adding thermally expandable spheres in an optically variable ink composition comprising optically variable pigment particles prior to applying said optically variable ink on said article or item to provide a marking having an irreversible change in color and/or a loss of color shifting property upon expansion of the thermally expandable spheres when subjected to a temperature increase of at least 35° C.

9. A method for detecting tampering activity of a marking on a substrate, the tampering activity comprising an increase of temperature of at least 35° C. and the marking including a tamper indicating marking comprising an optically variable ink comprising optically variable pigment particles and thermally expandable spheres configured to provide a marking having an irreversible change in color and/or a loss of color shifting property and/or a change in structure of the marking upon expansion of the thermally expandable spheres when subject to a temperature increase of at least 35° C., the method comprising detecting an irreversible change in color and/or a loss of color shifting property and/or a change in structure of the marking.

10. The method according to claim 9, wherein the irreversible change in color and/or a loss of color shifting property and/or the change in structure comprises the optically variable ink composition losing a color shifting property and/or a reduction in adhesion to the substrate.

11. The method according to claim 9, wherein the marking on a substrate is associated with an article.

12. The method according to claim 11, wherein the article is a high value document selected from any one of tax stamps, tax labels and banderols, or any one of a high value article selected from cosmetic articles, nutraceutical articles, pharmaceutical articles, alcohols, beverages or foodstuffs, electrical/electronics articles, fabrics and jewelry.

13. The method according to claim 8, wherein the optically variable pigment particles are selected from the group consisting of thin film interference pigment particles, interference coated pigment particles, cholesteric liquid crystal pigment particles and mixtures thereof.

14. A tamper indicating marking associated with an article comprising an optically variable ink composition, the optically variable ink composition comprising optically variable pigment particles and thermally expandable spheres, and the article is a high value document selected from the group consisting of tax stamps, tax labels and banderols or a high value article selected from the group consisting of cosmetic articles, nutraceutical articles, pharmaceutical articles, alcohols, beverages or foodstuffs, electrical/electronics articles, fabrics and jewelry.

15. A method for detecting tampering activity of a marking associated with an article, the tampering activity comprising an increase of temperature of at least 35° C. and the marking including an optically variable ink composition, the optically variable ink composition comprising optically variable pigment particles and thermally expandable spheres, and the article is a high value document selected from any one of tax stamps, tax labels and banderols, or any one of a high value article selected from cosmetic articles, nutraceutical articles, pharmaceutical articles, alcohols, beverages or foodstuffs, electrical/electronics articles, fabrics and jewelry.

16. The tamper indicating marking on a substrate according to claim 1, wherein the irreversible change in color and/or a loss of color shifting property comprises a loss of color shifting property.

17. The process according to claim 7, wherein the irreversible change in color and/or a loss of color shifting property comprises a loss of color shifting property.

18. The substrate or article comprising a tamper indicating marking according to claim 5, wherein the irreversible change in color and/or a loss of color shifting property comprises a loss of color shifting property.

19. The method according to claim 8, wherein the irreversible change in color and/or a loss of color shifting property comprises a loss of color shifting property.

20. The substrate or article comprising a tamper indicating marking according to claim 5, wherein the substrate or article is a high value article including alcohol.

21. The method according to claim 8, wherein the article or item is a high value article including alcohol.

22. The method according to claim 11, wherein the article is a high value article including alcohol.

23. The tamper indicating marking associated with an article according to claim 14, wherein the article is a high value article including alcohol.

24. The method according to claim 15, wherein the article is a high value article including alcohol.

* * * * *

UNITED STATES PATENT AND TRADEMARK OFFICE
CERTIFICATE OF CORRECTION

PATENT NO. : 9,605,167 B2  Page 1 of 1
APPLICATION NO. : 14/301883
DATED : March 28, 2017
INVENTOR(S) : T. Gazaway et al.

It is certified that error appears in the above-identified patent and that said Letters Patent is hereby corrected as shown below:

At Column 16, Line 38 (Claim 6, Line 3), "and article," should be -- an article, --.

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*